United States Patent [19]

Lugosi et al.

[11] Patent Number: 4,659,515

[45] Date of Patent: Apr. 21, 1987

[54] PROCESS FOR THE PREPARATION OF 6-DEMETHYL-6-DEOXY-6-METHYLENE-5-OXYTETRACYCLIN AND THE 11A-CHLORO-DERIVATIVE THEREOF

[75] Inventors: György Lugosi, Göd; Mária Hima née Toth, Budapest; Mária Bakonyi, Budapest; Sándor Szöke, Budapest, all of Hungary

[73] Assignee: Chinoin Gyogyszer es Vegyeszeti Termekek Gyara Rt, Budapest, Hungary

[21] Appl. No.: 646,574

[22] Filed: Aug. 31, 1984

[30] Foreign Application Priority Data

Sep. 2, 1983 [HU] Hungary ............................. 3061/83

[51] Int. Cl.$^4$ ............................................. C07C 103/19
[52] U.S. Cl. ................................. 260/351.5; 260/351.1
[58] Field of Search ........................... 260/351.5, 351.1

[56] References Cited

U.S. PATENT DOCUMENTS

| 2,984,686 | 5/1961 | Blackwood et al. | 260/351.1 |
| 3,200,149 | 8/1965 | Blackwood et al. | 260/351.1 |

FOREIGN PATENT DOCUMENTS

| 1283834 | 7/1969 | Fed. Rep. of Germany | 260/351.5 |
| 2037292 | 2/1971 | Fed. Rep. of Germany | 260/351.5 |
| 2232900 | 1/1973 | Fed. Rep. of Germany | 260/351.1 |
| 2131944 | 3/1973 | Fed. Rep. of Germany | 260/351.5 |
| 2533741 | 2/1976 | Fed. Rep. of Germany | 260/351.5 |
| 168392 | 2/1977 | Hungary | 260/351.5 |
| 169605 | 10/1977 | Hungary | 260/351.5 |
| 887671 | 1/1962 | United Kingdom | 260/351.5 |
| 995032 | 6/1965 | United Kingdom | 260/351.5 |

OTHER PUBLICATIONS

Merck Index, 9th Edition, 1976.

*Primary Examiner*—Glennon H. Hollrah
*Assistant Examiner*—Raymond Covington
*Attorney, Agent, or Firm*—Karl F. Ross; Herbert Dubno

[57] ABSTRACT

The invention relates to a new and improved process for the preparation of 6-demethyl-6-deoxy-6-methylene-5-oxytetracycline and the 11a-chloro derivative thereof by dehydrating 11a-chloro-5-oxytetracycline-6,12-hemiketal, which comprises treating 11a-chloro-5-oxytetracycline-6,12-hemiketal or an acid salt thereof with a dehydrating mixture formed by the reaction of chloro sulfonic acid and formic acid and isolating the 11a-chloro-6-demethyl-6-deoxy-6-methylene-5-oxytetracycline and salt thus obtained and optionally dehalogenating the same by reaction with a reducing agent.

The advantage of the process of the present invention is that it is simple, economical and suitable for industrial scale manufacture and provides a pure product of high quality by excellent yields.

6 Claims, No Drawings

PROCESS FOR THE PREPARATION OF 6-DEMETHYL-6-DEOXY-6-METHYLENE-5-OXYTETRACYCLIN AND THE 11A-CHLORO-DERIVATIVE THEREOF

This invention relates to a new and improved process or the preparation of 6-demethyl-6-deoxy-6-methylene-5-oxytetracycline and the 11a-chloro-derivative thereof.

According to the present invention there is provided a process for the preparation of 6-demethyl-6-deoxy-6-methylene-5-oxytetracycline and the 11a-chloro-derivative thereof by dehydrating 11a-chloro-5-oxytetracycline-6,12-hemiketal, which comprises treating 11a-chloro-5-oxytetracycline-6,12-hemiketale or an acid salt thereof with a dehydrating mixture formed by the reaction of chloro sulfonic acid and formic acid and isolating the 11a-chloro-6-demethyl-6-deoxy-6-methylene-5-oxytetracycline acid salt thus obtained and/or dehalogenating the same by reaction with a reducing agent.

11a-chloro-6-demethyl-6-deoxy-6-methylene-5-oxytetracycline is a valuable intermediate in the manufacture of tetracycline type antibiotics; the hydrochloric acid salt of 6-demethyl-6-deoxy-6-methylene-5-oxytetracycline is a well-known antibiotic (generic name: Metacycline). These compounds are generally prepared by dehydrating 11a-halogeno-5-oxytetracycline-6,12-hemiketal, isolating the 11a-halogeno-6-demethyl-6-deoxy-6-methylene-5-oxytetracycline generally in the form an acid salt thereof and converting the product thus obtained into 6-demethyl-6-deoxy-6-methylene-5-oxytetracycline by dehalogenation and isolating this compound either as the free base or in form of an acid salt. The key-step of the above synthesis is the dehydration reaction which can be carried out by several known methods. According to the most commonly used process anhydrous hydrogen fluoride is applied as dehydrating agent; this method yields the dehydrated compound with excellent yields in highly pure form. This process is disclosed e.g. in U.S. Pat. Nos. 2,984,686 and 3,200,149; German Federal Republic patent specifications Nos. 1,283,834 and 2,131,944; British patent specification No. 995,032 and and Hungarian patent specification No. 150,507. Beside the advantageous features this process is accompanied by serious drawbacks, namely the toxical properties of hydrogen fluoride and the strongly corrosive effect thereof towards metals, glass and enamelled surfaces. Hydrogen fluoride is a liquid which has a boiling point of 19.5° C. For this reason invention fluoride is rapidly converted into a gas at room temperature, it forms with the moisture content of air a nebulous (toxics) mixture; moreover it forms with air an explosive mixture. Hydrogen fluoride causes serious injuries to the eyes, the skin, the mucous membranes and the lungs; these cause very strong pain. The MAK-value of hydrogen fluoride amounts to 0.5 mg/m$^3$ which is practically that of hydrogen cyanide. Because of the very dangerous properties of hydrogen fluoride severe safety measures are to be taken in order to ensure the safe transport, storage and use of hydrogen fluoride which considerably increase the investment costs.

Several attempts were made to eliminate the use of hydrogen fluoride. Other dehydrating acids or acid derivatives were used, e.g. 90–95% sulfuric acid, 80–85% phosphoric acid, 60–70% perchloric acid, thionyl chloride, chloro sulfonic acid, alcoholic hydrochloric acid, a mixture of an organic acid and alkyl sulfonic acid (Hungarian patent specifications Nos. 150,507; 158,392 and 175,213; German Federal Republic patent specifications Nos. 1,283,834; 2,037,292; 2,131,944 and 2,533,741).

The above processes provide generally a lower yield than the hydrogen fluoride method and the quality of the product is lower too. For this reason in the said patent specifications often no yields are disclosed.

Hungarian patent specifications Nos. 168,392 and 175,213 are disclosed and discussed herein in a more detailed manner. According to Hungarian patent specification No. 168,392 dehydration is carried out with chloro sulfonic acid or sulfuric acid in the presence of nitro compounds. The yields given amount to about 90% for the crude product. The unsatisfactory purity of the product is proved by the fact that the yield of 11a-chloro-metacycline-tosylate is 80% and the product shows a strongly protracted melting pont (in the interval of 180°–220° C.). The use of nitrated solvents constitutes a further drawback because of health hazards and safety reasons. The isolation of the products is complicated since the use of nitrated solvents makes the precipitation of the product with ether necessary. This constitutes further problems of safety and economy: moreover the working up of the formed mixture comprising nitrated solvent, ether and acid represents an additional problem to be solved.

The process described in Hungarian patent specification No. 175,213 is encountered substantially with the same difficulties. The use of thionyl chloride requires the precipitation of the product with ether and the yield of 11a-chloro-metacycline-tosylate amounts to 65–81%. A further drawback is that in the reaction beside hydrogen chloride also gaseous sulfur dioxide is formed as by-product. Dehydration with sulfuric acid can only be carried out with a yield of 58%. A further disadvantage of the said procedures is that the products obtained generally contain in small amounts contaminations which are not present in the product obtained by the hydrogen fluoride process. For this reason the purification of the products obtained by the said methods is more complicated and expensive. Summarized it can be stated that none of the above procedure is competitive with the hydrogen fluoride process.

It has been found that when reacting formic acid with chloro sulfonic acid at a temperature below 0° C. hydrogen chloride is set free and a dehydrating agent—which contains presumably the mixed anhydride of formic acid and sulfonic acid—is formed which is excellently suitable for the dehydration of 11a-chloro-5-oxytetracyclin-6,12-hemiketal and provides the dehydrated product by very good yields in highly pure form. The reaction can be accomplished in a simple manner and the products can be isolated by various methods.

Reaction of formic acid and chloro sulfonic acid may be carried out at a temperature between 0° C. and −20° C. At higher temperature decomposition begins, while the use of lower temperature is unnecessary.

Dehydration may be preferably accomplished at a temperature between −20° C. and +30° C. Lower temperature do not give any additional advantage while at higher temperature decomposition takes place and the product becomes colored.

Formic acid has the additional advantages that when used in an excess it can play the role of the solvent as being an excellent reaction medium.

In the reaction as diluent inert solvents—preferably chlorinated solvents—may be used.

The dehydrating mixture can be prepared either before the addition of 11a-chloro-5-oxytetracycline-6,12-hemiketal or in the presence thereof.

In the prior art several methods are disclosed for dehalogenation. As examples of prior art citations U.S. Pat. Nos. 2,984,666 and 3,200,149; British patent specification No. 995,032; Hungarian patent specification No. 169,605 and Belgian patent specification No. 820,475 are referred to. In the said patent specifications reduction with zinc powder catalytic hydrogenation or reduction with a chemical reducing agents (e.g. sodium bisulfite or triphenyl phosphine) are disclosed.

It has been found that in the dehydration reaction a reaction mixture is obtained which is suitable for use in the dehalogenation reaction and for the isolation of the dehalogenated product in satisfactory purity without any isolation of the intermediates.

Further details of the present invention are to be found in the following Examples without limiting the scope of protection to the said Examples.

EXAMPLE 1

A mixture of 100 ml of formic acid and 100 ml of dichloro methane is cooled $-10°$ C. whereupon 27 ml of chloro sulfonic acid are added dropwise; hydrochloric acid is evolved. Under stirring and cooling within about 10–15 minutes 54.8 g (0.1 mole) of 11a-chloro-5-oxytetracycline-6,12-hemiketal-trihydrate are added. The solution this obtained is stirred at $-10°$ C. for an hour and at room temperature for 8 hours. The two phases formed are separated. The lower oily phase is extracted three times with 80 ml of dichloro methane each, stirred and separated. The lower oily phase is dissolved in 500 ml of isopropanol, 75 g of p-toluene sulfonic acid are added and the mixture is heated to boiling for 30 minutes. The precipitation of crystals begins soon. The mixture is crystallized by cooling at 0° C. for 2 hours. The crystals are filtered off, washed with acetone and dried. Thus 61 g of 11a-chloro-6-demethyl-6-deoxy-6-methylene-5-oxytetracycline-tosylate are obtained, yield 94%.

Mp.: 188°–189° C. (decomposition).

Cl% = 5.40 (calc.: 5.46).

H$_2$O < 1%.

IR spectrum: a characteristic band appears at 1780 cm$^{-1}$ which proves that the

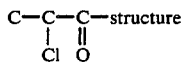

was formed i.e. dehydration took place.

EXAMPLE 2

54.8 g (0.1 mole) of 11a-chloro-5-oxytetracycline-6,12-hemiketal-trihydrate are dissolved in a mixture of 100 ml of dichloro methane and 100 ml of formic acid. Under stirring and cooling at $-10°$ C. a solution of 30 ml of chloro sulfonic acid and 100 ml of dichloro methane is added within about 10 minutes, whereupon the reaction mixture is stirred at $-10°$ C. for an hour and at room temperature for 8 hours. The two layers formed are separated from each other, the lower oily phase is extracted three times with 80 ml of dichloro methane each and separated. The oily phase is dissolved in 500 ml of isopropanol, 75 g of p-toluene sulfonic acid are added and the mixture is heated to boiling for 30 minutes. The precipitation of crystals begins soon. The mixture is crystallized by cooling to 0° C. for 2 hours, the crystals are filtered off, washed twice with 50 ml of acetone each and dried. Thus 61.6 g of 11a-chloro-6-demethyl-6-deoxy-6-methylene-5-oxytetracycline-tosylate are obtained, yield 95%.

EXAMPLE 3

A mixture of 80 ml of dichloro methane and 7.2 ml (0.19 mole) of formic acid is cooled to $-10°$ C., 12.7 ml (0.19 mole) of chloro sulfonic acid are added and at $-10°$ C. 22 g (0.04 mole) of 11a-chloro-5-oxytetracycline-6,12-hemiketal-trihydrate are added to the solution. A sticky heterogeneous reaction mixture is obtained which is difficult to be stirred. The reaction mixture is stirred at 0° C. for an hour and at room temperature for 24 hours. The liquid part is decanted, the stricky mass is taken up in 200 ml isoporpanol, 30 g of p-toluene sulfonic acid are added, the mixture is heated to boiling for 30 minutes and crystallized by cooling. Thus 22 g of 11a-chloro-6-demethyl-6-deoxy-6-methylene-5-oxytetracycline are obtained, yield 85%.

EXAMPLE 4

53 g (0.1 mole) of 11a-chloro-5-oxytetracycline-6,12-hemiketal-dihydrate are dissolved in a mixture of 100 ml of dichloro methane and 100 ml of formic acid. To the solution at $-10°$ C. within 10–15 minutes a solution of 19.8 ml of chloro sulfonic acid and 100 ml of dichloro methane is added. The reaction mixture is stirred at $-10°$ C. for an hour and at room temperature for 8 hours. The two layers formed are separated, the oily phase is extracted three times with 80 ml of dichloro methane each and separated. The oily phase is taken up in a solution of 26.2 g of triphenyl phosphine and 200 ml of methanol and heated to boiling whereupon 120 ml of concentrated hydrochloric acid are added. The mixture is crystallized by cooling, the crystals are filtered off, washed with acetone and dried. Thus 42 g of 6-demethyl-6-deoxy-6-methylene-5-oxytetracycline-hydrochloride are obtained, yield 88%.

According to thin layer chromatography the product is uniform and the amount of contaminations is below 1%.

$E_{490}^{1\ cm} = 0.035$; $E_{349}^{1\ cm} = 0.310$.

Biological activity: 977 U/mg.

The IR spectrum is identical with that of the standard.

EXAMPLE 5

5.3 g (0.01 mole) of 11a-chloro-5-oxytetracycline-6,12-hemiketal-dihydrate are dissolved in a mixture of 10 ml of dichloro methane and 10 ml of formic acid whereupon at $-10°$ C. a solution of 2 ml of chloro sulfonic acid and 10 ml of dichloro methane is added dropwise. The reaction mixture is stirred at $-10°$ C. for an hour and at room temperature for 5 hours. The two layers are separated, the oily phase is extracted twice with 10 ml of dichloro methane each, the oily phase is separated and the solvent is distilled off in vacuo. The residue is taken up in a mixture of 20 ml of methanol and 10 ml of concentrated hydrochloric acid, whereupon 5.4 g of sulfosalicyclic acid and 1 g of zinc power are added. The mixture is stirred at 35°–40° C. for 5 hours and crystallized by cooling with ice. Thus 5 g of 6-demethyl-6-deoxy-6-methylene-5-oxytetracycline-sulfosalicylate are obtained.

EXAMPLE 6

28.57 g (0.05 mole) of 11a-chloro-5-oxytetracyclin-6,12-hemiketal-hydrochloride-monohydrate are dissolved in a mixture of 50 ml of formic acid and 35 ml of dichloro methane, whereupon a solution of 9.5 ml of chloro sulfonic acid and 10 ml of dichloro methane is added dropwise at −10° C. The reaction mixture is stirred at −10° C. for an hour and at room temperature for 5 hours. To the mixture 250 ml of isoporpanol and 37.5 g of p-toluene-sulfonic acid are added. The mixture is heated to boiling for 30 minutes and crystallized by cooling at 0° C. for 2 hours. The crystals are filtered off, washed with acetone and dried. Thus 31 g of 11a-chloro-6-demethyl-6-deoxy-6-methylene-5-oxytetracycline-tosylate are obtained, yield 95%.

What we claim is:

1. A process for the preparation of a compound selected from the group consisting of 6-demethyl-6-deoxy-6-methylene-5-oxytetracycline and 11a-chloro-6-demethyl-6-deoxy-6-methylene-5-oxytetracycline or a pharmaceutically acceptable acid addition salt thereof in a yield of at least 85% and in pure form, which comprises treating 11a-chloro-5-oxytetracycline-6,12-hemiketal or a pharmaceutically acceptable acid addition salt thereof with a dehydrating mixture formed by the reaction of chlorosulfonic acid and formic acid and isolating the 11a-chloro-6-demethyl-6-deoxy-6-methylene-5-oxytetracycline or the pharmaceutically acceptable acid addition salt thereof thus obtained, or optionally dehalogenting the 11a-chloro-6-demethyl-6-deoxy-6-methylene-5-oxytetracycline or the pharmaceutically acceptable acid addition salt thereof by reaction with a reducing agent, to yield the 6-demethyl-6-deoxy-6-methylene-5-oxytetracycline or the pharmaceutically acceptable acid addition salt thereof.

2. Process according to claim 1, which comprises carrying out the reaction of chloro sulfonic acid and formic acid at a temperature between 0° C. and −20° C.

3. Process according to claim 1, which comprises preparing the dehydrating mixture directly in the reaction mixture.

4. Process according to any of claim 1, which comprises carrying out the dehydration reaction at a temperature between −20° C. and +30° C.

5. Process according to any of claim 1, which comprises using an excess of formic acid as solvent.

6. Process according to any of claim 1, which comprises carrying out the dehydrating step in the presence of an inert solvent as diluent.

* * * * *